(12) United States Patent
Ingimundarson et al.

(10) Patent No.: US 8,282,588 B2
(45) Date of Patent: Oct. 9, 2012

(54) ORTHOPEDIC DEVICE HAVING HYBRID FRAME ELEMENTS

(75) Inventors: Arni Thor Ingimundarson, Ladera Ranch, CA (US); Palmi Einarsson, San Juan Capistrano, CA (US)

(73) Assignee: Ossur Hf, Reykjavik (IS)

( * ) Notice: Subject to any disclaimer, the term of this patent is extended or adjusted under 35 U.S.C. 154(b) by 323 days.

(21) Appl. No.: 12/628,264

(22) Filed: Dec. 1, 2009

(65) Prior Publication Data
US 2010/0137766 A1    Jun. 3, 2010

Related U.S. Application Data

(60) Provisional application No. 61/119,441, filed on Dec. 3, 2008.

(51) Int. Cl.
*A61F 5/00* (2006.01)
(52) U.S. Cl. .............. 602/16; 602/5; 602/23; 602/26; 602/27
(58) Field of Classification Search ............... 602/5, 15, 602/23, 26–29, 16, 20; 128/878–879, 882
See application file for complete search history.

(56) References Cited

U.S. PATENT DOCUMENTS

| | | |
|---|---|---|
| 4,256,097 A | 3/1981 | Willis |
| 4,691,697 A | 9/1987 | Arensdorf et al. |
| RE32,650 E | 4/1988 | Waddell |
| 5,007,415 A | 4/1991 | Marion |
| 5,547,464 A | 8/1996 | Luttrell et al. |
| 5,653,680 A | 8/1997 | Cruz |
| 5,733,249 A | 3/1998 | Katzin et al. |
| 5,951,504 A | 9/1999 | Iglesias et al. |
| 6,080,123 A | 6/2000 | Pansiera |
| 6,102,881 A | 8/2000 | Quackenbush et al. |
| 6,129,690 A | 10/2000 | Hamlin et al. |
| 6,245,034 B1 | 6/2001 | Bennett et al. |
| 6,409,693 B1 | 6/2002 | Brannigan |
| 6,409,695 B1 | 6/2002 | Connelly |
| 6,471,664 B1 | 10/2002 | Campbell et al. |
| 6,537,237 B1 | 3/2003 | Hopkins et al. |
| 6,589,195 B1 | 7/2003 | Schwenn et al. |
| 6,635,024 B2 | 10/2003 | Hatton et al. |
| 6,752,774 B2 | 6/2004 | Townsend et al. |
| 6,824,523 B2 | 11/2004 | Carlson |
| 6,839,906 B2 | 1/2005 | Gold et al. |

(Continued)

FOREIGN PATENT DOCUMENTS

EP        1714 62 3 A2    10/2006

(Continued)

OTHER PUBLICATIONS

International Search Report issued in related application PCT/US2009/006238, May 3, 2010.

*Primary Examiner* — Kim M Lewis
(74) *Attorney, Agent, or Firm* — Bacon & Thomas, PLLC

(57) ABSTRACT

An orthopedic device includes a rigid or substantially rigid frame element having a first thickness and a periphery, and an overmolded portion surrounding at least a peripheral segment of the frame element periphery. The overmolded portion encases the thickness of the peripheral segment and interlocks with the frame element without fastener elements. The combination of the frame element and the overmolded portion are adapted to secure against an anatomical portion.

20 Claims, 2 Drawing Sheets

U.S. PATENT DOCUMENTS

| | | |
|---|---|---|
| 6,936,020 B2 | 8/2005 | Davis |
| 6,969,363 B2 | 11/2005 | Houser |
| 6,969,365 B2 | 11/2005 | Scorvo |
| 7,033,330 B2 | 4/2006 | de Lint |
| 7,048,704 B2 | 5/2006 | Sieller et al. |
| 7,083,583 B2 | 8/2006 | Opahle et al. |
| 7,112,180 B2 | 9/2006 | Guenther |
| 7,150,721 B2 | 12/2006 | Houser |
| 7,207,960 B2 | 4/2007 | Kenney |
| 7,309,322 B2 | 12/2007 | Albrecht et al. |
| 7,918,809 B2 * | 4/2011 | Enzerink et al. ............... 602/16 |
| 2003/0093018 A1 | 5/2003 | Albrecht et al. |
| 2004/0260220 A1 | 12/2004 | Wagner et al. |
| 2005/0033208 A1 | 2/2005 | Jacobs |
| 2005/0165338 A1 | 7/2005 | Iglesias et al. |
| 2006/0046910 A1 | 3/2006 | Rastegar et al. |
| 2006/0142680 A1 | 6/2006 | Iarocci |
| 2006/0206043 A1 | 9/2006 | Yakimovich et al. |
| 2006/0264790 A1 | 11/2006 | Kruijsen et al. |
| 2007/0021842 A1 | 1/2007 | Oddsson et al. |
| 2007/0038168 A1 | 2/2007 | Turrini et al. |
| 2007/0232972 A1 | 10/2007 | Martinez |
| 2008/0294083 A1 | 11/2008 | Chang et al. |

FOREIGN PATENT DOCUMENTS

| | | |
|---|---|---|
| GB | 24 3 6799 A | 10/2007 |
| WO | 82/02658 | 8/1982 |

* cited by examiner

ORTHOPEDIC DEVICE HAVING HYBRID FRAME ELEMENTS

CROSS-REFERENCE TO RELATED APPLICATIONS

This application claims the benefit of U.S. provisional application No. 61/119,441, filed on Dec. 3, 2008, incorporated herein by reference.

FIELD OF THE INVENTION

The invention pertains to the field of the orthopedic devices, and more particularly to orthopedic devices having interlocking frame elements requiring different material properties.

BACKGROUND

Orthopedic devices employ a variety of connections among different elements such as shells adapted to secure about an anatomical portion, hinges permitting articulation of a limb, and struts carrying straps. Difficulties arise in assembling these elements in that it is time consuming and expensive. Moreover, machining these elements also adds to the cost and time of manufacturing such devices, and in many instances the assembly of such devices requires a variety of different fasteners.

SUMMARY

In accordance with a first embodiment of the invention, an orthopedic device includes a rigid or substantially rigid frame element having a first thickness and a periphery, and an overmolded portion surrounds at least a peripheral segment of the frame element periphery. The overmolded portion encases the thickness of the peripheral segment and securely interlocks with the frame element without the need for any fastener-type elements. The combination of the frame element and the overmolded portion are adapted to secure against an anatomical portion.

Turning to the overmold portion, it preferably has greater flexibility than the frame element. The overmolded portion also defines at least one elongate opening adapted to receive a strap. In accordance with a variation, the overmolded portion defines a variable thickness region having a thinned segment such that the thinned segment is resilient upon bending thereby permitting flexure of the overmolded portion.

In a variation, a flange may extend from the overmolded portion with the flange connecting to the overmolded portion via a living hinge. The flange defines at least one elongate opening adapted to receive a strap.

The overmolded portion and the frame element have interlocking features thereby integrally securing the frame element to the overmolded portion. The overmolded portion is preferably a polymeric material. The frame element may be a carbon-fiber based composite, or a metallic plate. In a variation of the embodiment, the device defines at least one opening extending through the frame element and the overmolded portion. The frame element may define an aperture and the material of the overmolded portion extends through the aperture.

In another embodiment, the device includes first and second rigid or substantially rigid frame elements spaced apart from one another. The overmolding portion connects the first and second frame elements to one another. In a variation, a second overmolded portion extends about a peripheral segment of the overmolded portion. The second overmolded portion is preferably more flexible than the overmolded portion.

These and other features, aspects, and advantages of the present invention will become better understood with regard to the following description, appended claims, and accompanying drawings.

DETAILED DESCRIPTION OF VARIOUS EMBODIMENTS

A. Overview

Figure 1:
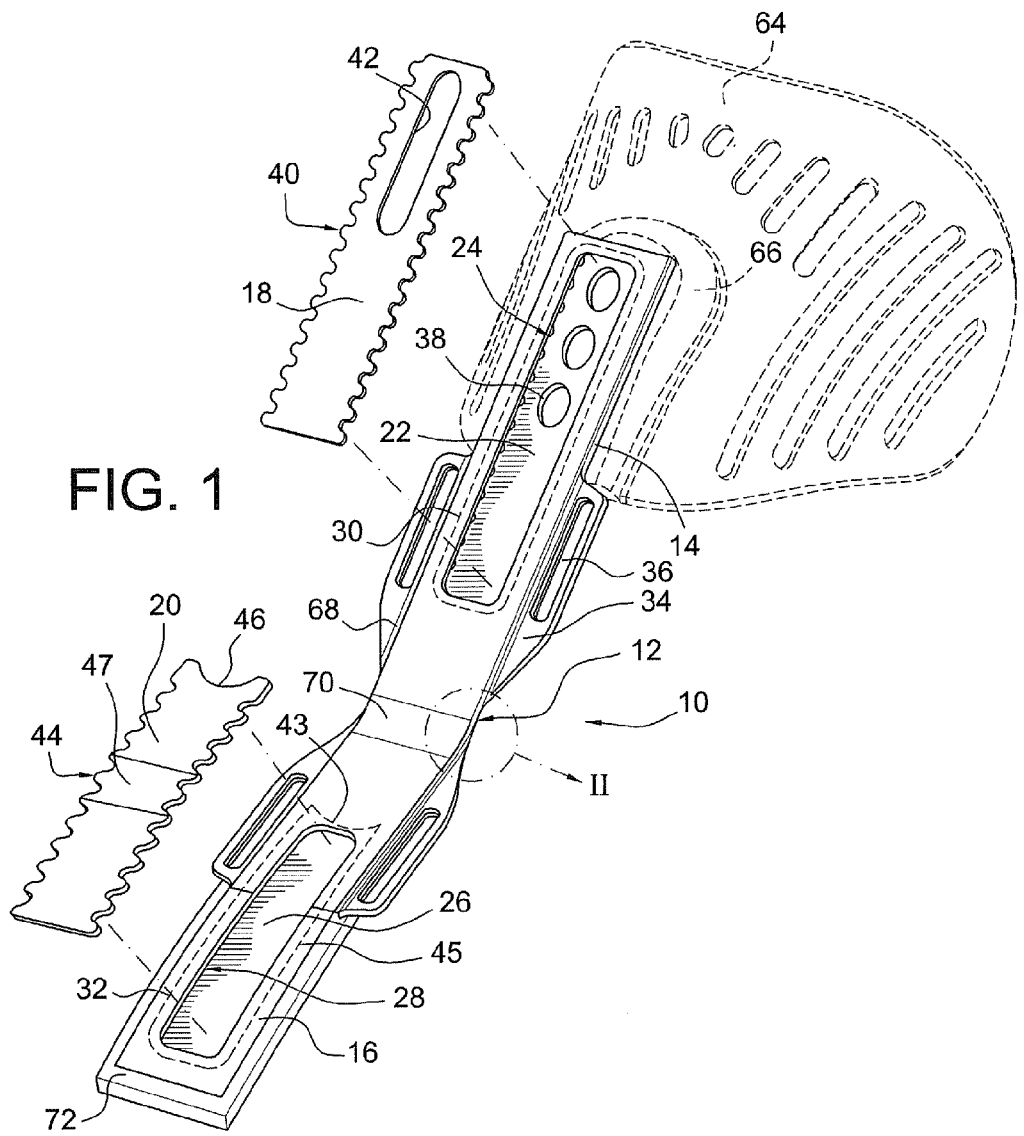
FIG. 1 is a perspective exploded view showing a first embodiment of an orthopedic device having hybrid frame elements.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Orthopedic Brace and Components for Use Therewith

In observing FIG. 1, an embodiment of a frame assembly 10 having hybrid elements is shown. The assembly 10 is shown in the form of a strut and includes an overmold connecting portion 12 and first and second overmold portions 14, 16 continuously extending from the connecting portion 12. A first rigid insert 18 and a second rigid insert 20 (in this embodiment, upper and lower, respectively) are securely received in respective first overmold and second mold cavities 22, 26. The inserts are rigid or substantially rigid, in particular as compared to the overmold portions. The overmold portions, on the other hand, may be rigid or substantially rigid, but are less rigid than the inserts.

The overmolded portions 14, 16 encase a thickness of the periphery of the rigid inserts 18, 20 such that the overmolded portions interlock with the frame elements. The peripheries of the rigid inserts 18, 20 are encased by edges of the overmold portions which extend over the periphery of a top surface of the upper and lower cavities 30, 32. The overmold portions 14, 16 define a plurality of receiving portions 24, 28, which interlock with first and second locking tabs 40, 44 of the first and second inserts 18, 20.

In this embodiment, a rear surface of the inserts is located adjacent a surface of the overmold, whereas as a front surface of the inserts is at least partially exposed. It will be noted, however, that the inserts may be fully encased within the overmold such that both the front and rear surfaces are covered by the overmold.

The assembly 10 includes flanges 34 which protrude outwardly from the first and second overmold portions 14, 16. These flanges 34 are connected to the overmold portions 14, 16 via living hinges 68 which permit deflection of the flanges 34 relative to the overmold portions 14, 16. The flanges 34 each define an opening 36 which is adapted to receive a strap. Preferably, corresponding flanges 34 are provided on opposed sides of the overmold portions 14, 16 so as to receive opposed ends of a strap (not shown).

The inserts 18, 20 may define numerous features, such as an elongate slot 42 in the first insert 18 which corresponds to a plurality of openings 38 feinted by the first overmold portion 14. The second insert 20 defines an arcuate recessed portion 46 along an end portion which corresponds to an arcuate section 43 of the cavity 26. Further, the second insert 20 includes a contoured bend 47 which corresponds to a contoured bend 45 defined by the second overmold portion 16.

A third overmold portion 72 extends around the periphery of the second overmold portion 16. The third overmold portion 72 may be integrally secured to the second overmold portion 16, and it has greater softness and flexibility than the second overmold portion 16. The third overmold portion may be formed with the second overmold portion as is described in pending U.S. patent application Ser. No. 11/312,416.

A shell 64 may be attached to either one of the combinations of the first overmold and insert, and second overmold and insert. Such shell 64 may include a housing 66 which has adjustable means for adjusting the height of the shell 64 on an end portion of the overmold/insert combination.

Figure 2:
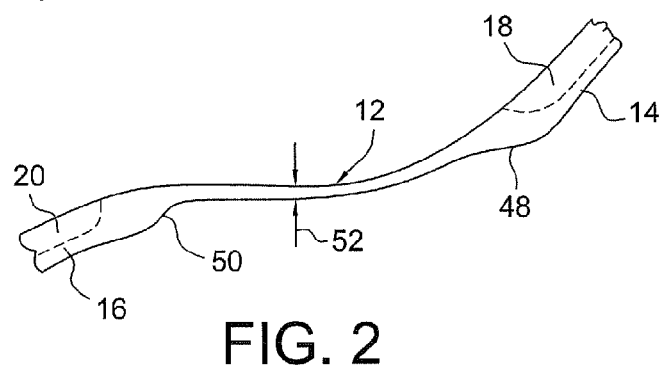
FIG. 2 is an exemplary cross-sectional view showing the connecting portion of the orthopedic device of FIG. 1.

Turning to FIG. 2 which depicts a detailed view of the connecting portion 12 bridging between the first and second overmold portions 14, 16. The connecting portion 12 serves as a living hinge in that it has a thickness 52 which is less than the thickness of the first and second overmold portions 14, 16. The connecting portion 12 defines transitional thickness portions 48, 50 which provide a gradual transition between the thickness 52 and the thicknesses of the overmold portions 14, 16.

The thickness 52 is preferably of a degree that allows the overmold portions 14, 16 to bend relative to one another. Moreover, the material forming the connecting portion 12 allows for the connecting portion to be resilient thereby permitting connecting portion to flex while returning to its molded shape.

Figure 3:
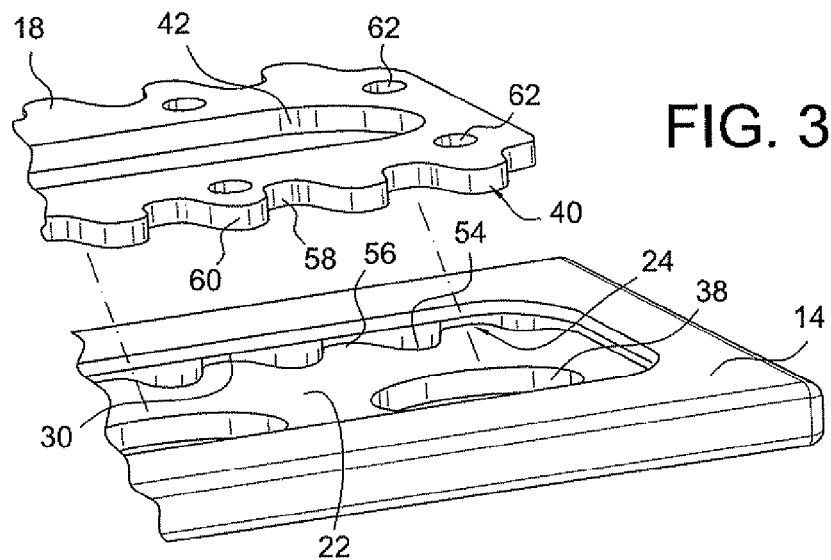
FIG. 3 is an exemplary exploded view showing a frame element and a rigid insert.

FIG. 3 depicts the receiving portions 24 of the first overmold portion 14 as having alternating crests 54 and indentations 56 which correspond to indentations 58 and crests 60, respectively, of the locking tabs 40 of the first insert 18. Apertures 62 are formed in the first insert 18 which interlock with material of the overmold portion. This arrangement of the receiving portions 24 and the locking tabs 40 allows for the insert to be fixably secured within the cavity 22, in combination with the encasement of the insert 18 by the edge 30 which extends over the top surface periphery of the insert.

Preferably, the overmolded portions comprise a polymeric material that is molded over the inserts, and formed to shape by a mold. This permits the inserts to be secured by the overmold portions without the necessity of fasteners. For example, the insert may be placed in a mold and injection molded polymeric material flows around portions of the insert in accordance with the depiction of FIG. 1. The polymeric material will flow into the apertures 62 and around the locking tabs 40, and tightly form there around.

Of course, it will be understood other means are available to the skilled person for overmolding the overmold portions about the inserts, and retaining the inserts by the overmold portions. The above-noted structure in reference to FIG. 3 is merely provided by way of example.

The overmold portions may be constructed from a variety of materials such as TRIAX (abs/nylon blend), polypropylene, polyethylene, nylon, carbon or glass fiber prepeg with thermosetting or thermoplastic resins, and rigid foam from EVA, platezote or polyurethane. The inserts may be constructed from a variety of material including metals such as aluminum, titanium, and steel, thermoset resin composite systems including glass or carbon fibers, and thermoplastics that have been rendered rigid by way of material composition and geometry of the frame members.

Figure 4:
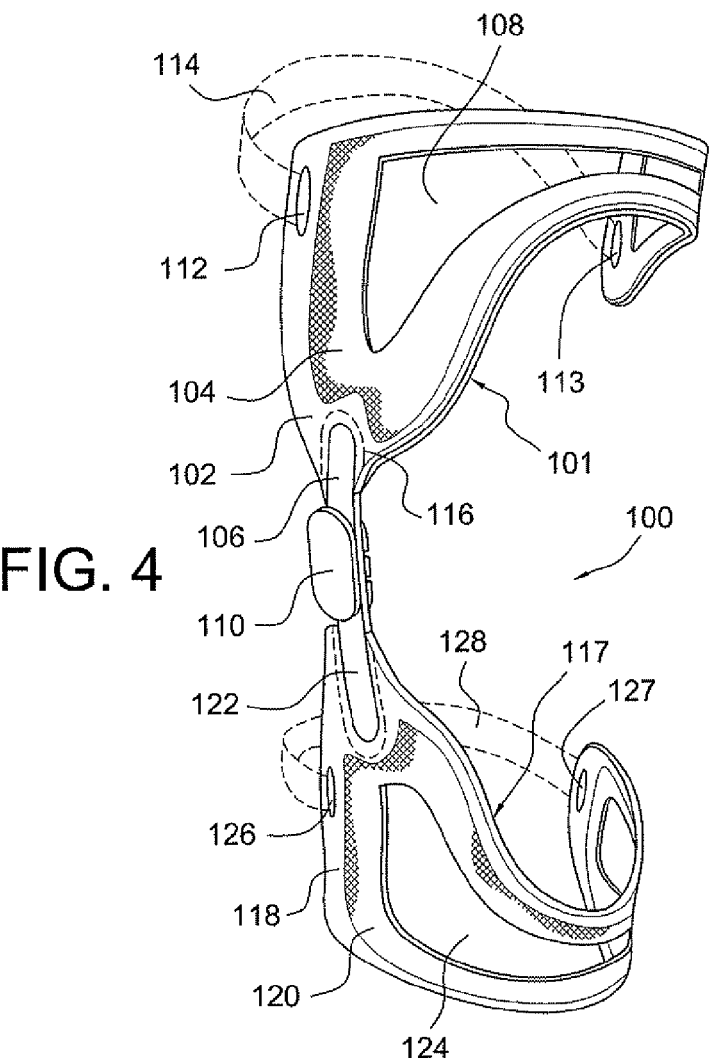
FIG. 4 is a perspective view showing a second embodiment of an orthopedic device having hybrid frame elements.

In observing FIG. 4, another embodiment of a frame assembly 100 having hybrid elements is shown. This assembly 100 defines an upper subassembly 101 having a first overmold portion 102 which extends around a first insert 104 having an opening 108, and a second insert 106. The first and second inserts 104, 106 are preferably spaced apart from one another by a distance such that the overmold portion 102 connects these first and second inserts 104, 106 to one another. The overmold portion 102 defines opposed slots 112, 113 that are arranged to receive opposite ends of a strap 114.

A hinge 110 connects the upper frame subassembly 101 to a lower subassembly 117. The lower subassembly 117 has a second overmold portion 118 which extends around a third insert 120 having an opening 124, and a fourth insert 122. The third and fourth inserts 120, 122 are preferably spaced apart from one another by a distance such that the second overmold portion 118 connects these third and fourth inserts 120, 122 to one another. The actual periphery of the second and fourth inserts 106, 122 is denoted by reference number 116 as being embedded in the overmold. The second overmold portion 118 defines opposed slots 126, 127 that are arranged to receive opposite ends of a strap 128.

In accordance with this embodiment, the first and third inserts 104, 120 are preferably formed by carbon-fiber reinforced composites. The second and the fourth inserts 106, 122 are preferably aluminum plates which can couple to the hinge 110, or have components which are machined accordingly to form part of the hinge.

Advantageously with this embodiment, there is no need for any fasteners since the first and third inserts are coupled to the second and fourth inserts, respectively, by the overmold portions. The overmold portions serve to connect these inserts to one another, and thus the reason they are preferably spaced from one another. Moreover, because the overmold portions are easily molded, the slots are formed when the overmold portions are formed over the inserts, thereby removing the need for machining of slots.

While the foregoing embodiments have been described and shown, it is understood that alternatives and modifications of these embodiments, such as those suggested by others, may be made to fall within the scope of the invention.

It will be further understood that any of the concepts advanced herein may be extended to suitable prosthetic devices or any other device requiring such hybrid frame elements.

The invention claimed is:

1. An orthopedic device, comprising:
a rigid frame element having a first thickness and a periphery forming a plurality of tabs with indentations spaced therebetween;
an overmolded portion having a rigid or semi-rigid section surrounding at least a peripheral segment of the frame element and filling the indentations of the frame element, the section encasing the thickness of the peripheral segment, the overmolded portion securely interlocking with the frame element without any fasteners;
wherein the combination of the frame element and the overmolded portion are adapted to secure against anatomy of a wearer of the device.

2. The device according to claim 1, wherein the overmolded portion has greater flexibility than the frame element.

3. The device according to claim 1, wherein the overmolded portion defines at least one elongate opening adapted to receive a strap.

4. The device according to claim 1, wherein the overmolded portion defines a variable thickness region having a thinned segment, the thinned segment being resilient upon bending thereby permitting flexure of the overmolded portion.

5. The device according to claim 1, further comprising a flange extending from the overmolded portion, the flange connecting to the overmolded portion via a living hinge.

6. The device according to claim 5, wherein the flange defines at least one elongate opening adapted to receive a strap.

7. The device according to claim 1, wherein the overmolded portion is a polymeric material.

8. The device according to claim 1, wherein the frame element is a carbon-fiber based composite.

9. The device according to claim 1, wherein the frame element is a metallic plate.

10. The device according to claim 1, wherein the device defines at least one opening extending through the frame element and the overmolded portion.

11. The device according to claim 1, wherein the frame element defines an aperture, the material of the overmolded portion extends through the aperture.

12. The device according to claim 1, further comprising first and second rigid or substantially rigid frame elements spaced apart from one another, the overmolding portion connecting the first and second frame elements.

13. An orthopedic device, comprising:
at least two rigid frame elements each having a thickness and a periphery;
an overmolded portion surrounding at least a peripheral segment of the peripheries of the frame elements, the overmolded portion encasing the thickness of the peripheral segment, the overmolded portion securely interlocking with the frame elements without any fasteners, whereby the combination of the frame element and the overmolded portion are adapted to secure against anatomy of a wearer of the device;
wherein the frame elements are separated by one another by a connecting section of the overmolded portion that continuously extends between the at least two frame elements;
wherein the connecting section defines a variable thickness region having a thinned segment, the thinned segment being resilient upon bending thereby permitting flexure of the connecting section.

14. The orthopedic device according to claim 13, wherein at least one of the frame elements is formed from one of the materials selected from the group consisting of carbon fiber and aluminum.

15. The orthopedic device according to claim 13, wherein the overmolded portion comprises a polymeric material.

16. The orthopedic device according to claim 13, wherein the frame element has a first thickness and a periphery forming a plurality tabs with indentations spaced therebetween.

17. The orthopedic device according to claim 16, wherein the overmolded portion is formed from a polymeric material having a rigid or semi-rigid section surrounding and filling the indentations of the frame element.

18. A strut comprising:
a rigid frame element having a first thickness and a periphery forming a plurality tabs with indentations spaced therebetween;
an overmolded portion formed from a polymeric material having a rigid or semi-rigid section surrounding at least a peripheral segment of the periphery and filling the indentations of the frame element, the section encasing the thickness of the peripheral segment, the overmolded portion securely interlocking with the frame element without any fasteners, the overmolded portion having portions of varying thickness;
wherein the rigid frame element has greater rigidity than the overmolded portion.

19. The strut according to claim 18, wherein the overmolded portion defines a variable thickness region having a thinned segment, the thinned segment being resilient upon bending thereby permitting flexure of the overmolded portion.

20. The orthopedic device according to claim 1, wherein a rear surface of the frame element is adjacent a surface of the overmolded portion and a front surface of the frame element is at least partially exposed.

* * * * *